United States Patent [19]

Gahara et al.

[11] Patent Number: 4,995,865
[45] Date of Patent: Feb. 26, 1991

[54] MULTI-LUMEN CATHETERS

[75] Inventors: William J. Gahara, Nashua; Thomas R. Johnson, Milford, both of N.H.

[73] Assignee: Worldwide Medical Plastics Inc., Nashua, N.H.

[21] Appl. No.: 364,799

[22] Filed: Jun. 9, 1989

[51] Int. Cl.$^5$ .............................. A61M 5/00
[52] U.S. Cl. ...................... 604/43; 604/53; 604/280
[58] Field of Search .............. 604/93, 96–99, 604/101–102, 264, 43–45, 53, 280, 283, 284, 27, 158

[56] References Cited

U.S. PATENT DOCUMENTS

| | | |
|---|---|---|
| 272,651 | 2/1884 | Mahurkar. |
| 3,411,506 | 11/1968 | Velasco ................ 604/101X |
| 3,848,602 | 11/1974 | Gutnick ................ 606/193 |
| 4,568,329 | 2/1986 | Mahurkar. |
| 4,583,968 | 4/1986 | Mahurkar. |
| 4,692,141 | 9/1987 | Mahurkar. |
| 4,763,654 | 8/1988 | Jang ................ 604/101X |
| 4,795,439 | 1/1989 | Guest ................ 604/43 |
| 4,894,057 | 1/1990 | Howes ................ 604/280 |

Primary Examiner—C. Fred Rosenbaum
Assistant Examiner—Corrine Maglione
Attorney, Agent, or Firm—St. Onge Steward Johnston & Reens

[57] ABSTRACT

Catheters having three lumens for injection and removal of fluids comprise an elongated tube having an integrally formed septum which extends throughout the length of the tube and defines the three lumens which may have the same or different cross-sectional areas. A smooth conical tapered tip is provided at the distal end of the tube and one of the lumens extends continuously through the tip to an opening at the apex of the tip. The other lumens extend continuously from the proximal end of the tube to openings in their sidewalls at a location axially spaced from the tip at the distal end. These catheters permit higher rates of fluid transfer in dialysis and like procedures than do double lumen catheters and are less prone to occlusion.

15 Claims, 2 Drawing Sheets

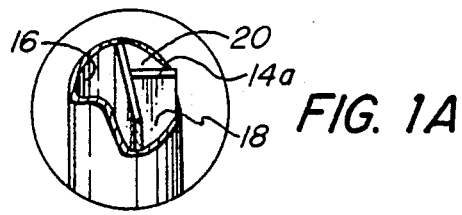
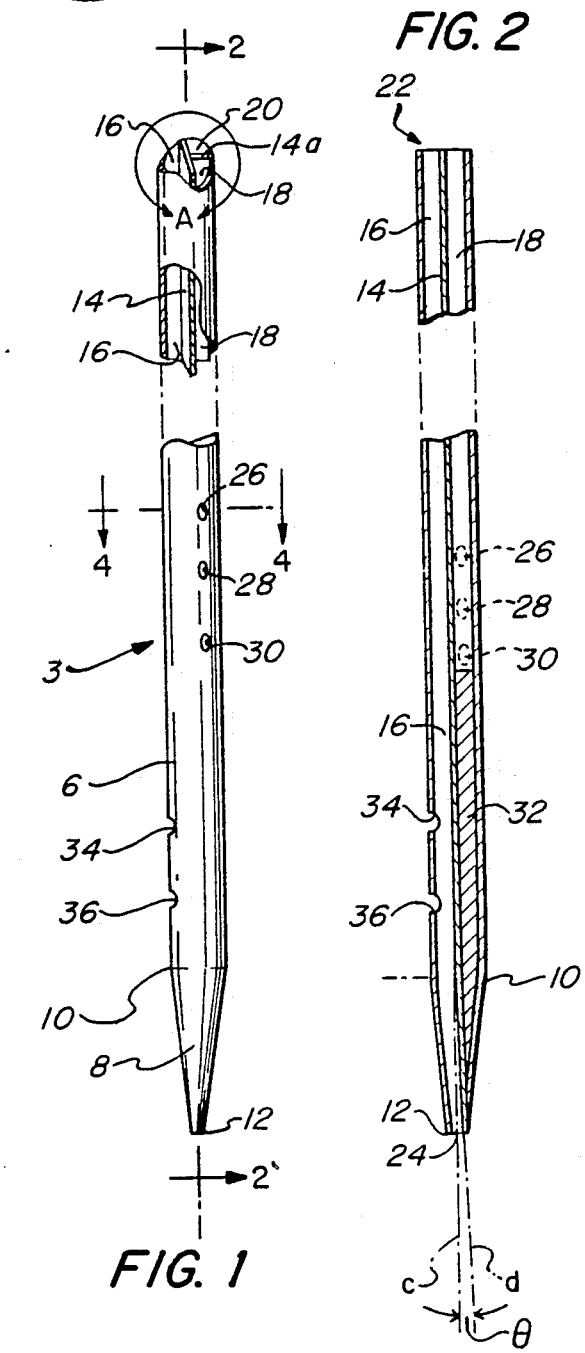
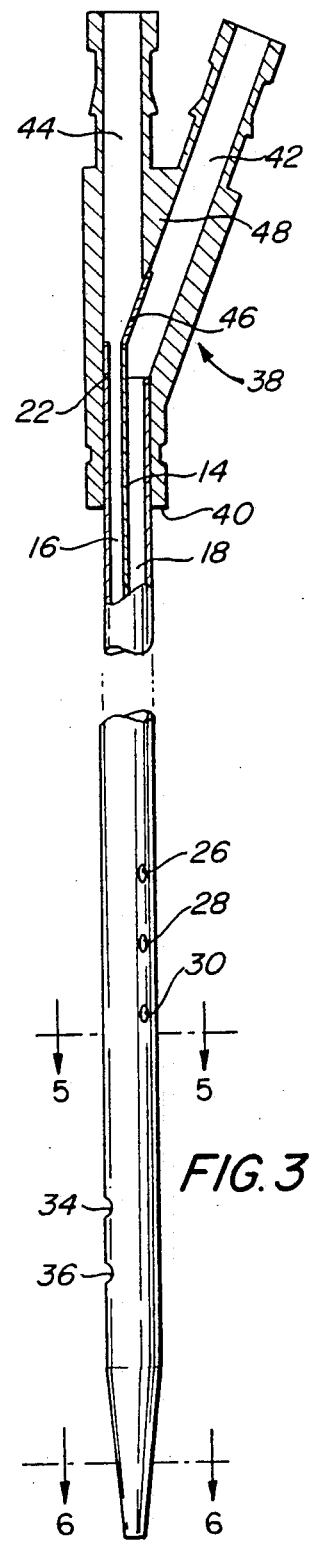

MULTI-LUMEN CATHETERS

BACKGROUND OF THE INVENTION

1. Field of the Invention

This invention relates to devices for withdrawing fluids from and/or introducing fluids into a cavity or vessel of the body and is more particularly concerned with improvements in multi-lumen catheters and with methods for their fabrication.

2. Description of the Prior Art

Double lumen catheters, also known as double current catheters, are well-known in the art and are widely used in medical procedures such as hemodialysis and the like. In such procedures fluid is introduced through one of the lumens into a vein or other vessel while a corresponding amount of fluid is withdrawn through the other lumen. Typical of double lumen catheters currently available are those described by Mahurkar in U.S. Pat. Nos. 4,568,329; 4,583,968; and 4,692,141 as well as U.S. Pat. No. Des. 272,651. The '329 patent describes a catheter comprising an elongated tube divided into two lumens having semi-circular cross-sections by an integral septum which extends throughout the length of the tube. At the distal end of the catheter one of the lumens opens through a bevelled aperture. The other lumen extends into a second cylindrical portion of enlarged diameter in the transverse direction normal to the plane of the septum, which portion terminates in a conical tapered tip. The '141 patent is based on a continuation of the '329 patent and describes a variation of the structure of the above second portion of the catheter. The Des. Patent shows a similar tip except that the second cylindrical portion does not have the enlarged diameter described in the '329 and '141 patents.

The '968 patent describes a double lumen catheter having a different tip portion. The two lumens are of semi-circular cross-section as before and extend throughout the length of catheter. The distal end of the catheter has a smooth conical tip which merges smoothly with the exterior surface of the tube. One of the lumens extends into and through the tip portion and terminates in an opening in the apex of the tip. The other lumen terminates in an opening in its sidewall at a location which is axially displaced from the conical tip. The remainder of this other lumen, which would otherwise extend into the tip, is blocked off by solid material. This latter feature is said to provide rigidity so that the tip functions as an effective dilator for soft tissue and veins.

The present invention is directed to three-lumen catheters which possess a number of advantages over two-lumen catheters.

SUMMARY OF THE INVENTION

It is an object of the invention to provide multi-lumen catheters having improved structure and performance characteristics.

It is another object of the invention to provide a three-lumen catheter which can yield improved performance when employed in dialysis and like procedures.

These objects, and other objects which will be apparent from the description which follows, are achieved by the catheter devices of the present invention. The latter in its broadest aspect comprises a three-lumen catheter which takes the form of an elongated unitary tube having an integral septum extending within the entire length of the tube and dividing the interior of the latter into three lumens. At its distal end the outer surface of the tube converges smoothly to form a conical tapered tip. One of the lumens extends continuously from the proximal end of the tube through the conical tapered tip to an opening in the apex of the tip. The other lumens have at least one opening in the side thereof at a location axially spaced from the conical tapered tip. The remainder of these lumens between said openings and the tapered tip are blocked off.

In a particular embodiment the integral septum has an approximately T-shaped cross-section giving rise to a first lumen having an approximately semi-circular cross-section and second and third lumens having approximately quadrantal cross-sections. The first lumen is the one which extends through the conical tapered tip to an opening in the apex of the tip.

It has been found that the septum in the catheters of the invention provides enhanced structural strength to the tip of the catheter and enables the tip to function as an effective dilator for veins and the like into which it is inserted. It has also been found that, by using the second and third lumens together to withdraw fluid and using the first lumen to introduce fluid it is possible to achieve higher rates of fluid transfer in dialysis and like procedures with significantly less chance of occlusion of the side ports than is the case using double lumen catheters. It has been found further that the conical tapered tips of the catheters of the invention can be fabricated with greater accuracy and ease of reproducibility than similar tips heretofore described.

BRIEF DESCRIPTION OF THE DRAWINGS

FIG. 1 is a side elevational view, partially cutaway, of a three-lumen catheter in accordance with the invention.

FIG. 1A is an enlarged view of a section of the catheter of FIG. 1.

FIG. 2 is a cross-sectional view, taken along the line 2—2 which is fractionally offset from the plane of the longitudinal axis, of the three-lumen catheter shown in FIG. 1.

FIG. 3 is a side elevational view, partially cutaway, of a three-lumen catheter with attached branching connector in accordance with the invention.

DETAILED DESCRIPTION OF THE INVENTION

Figure 4:
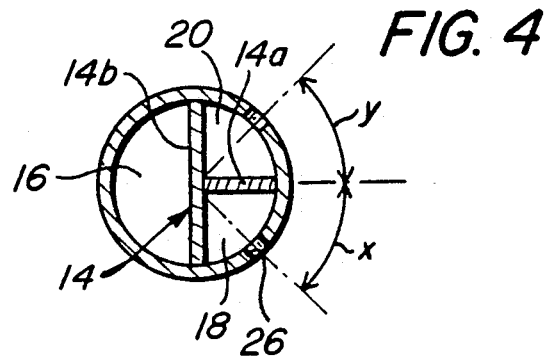
FIG. 4 is a cross-sectional view taken along line 4—4 of the catheter shown in FIG. 1.
Figure 5:
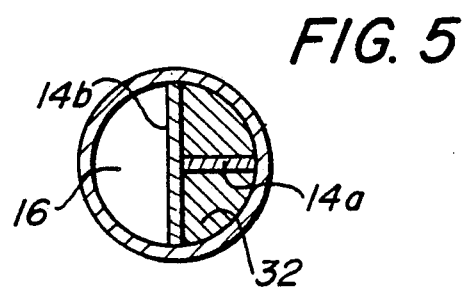
FIG. 5 is a cross-sectional view taken along line 5—5 of the catheter shown in FIG. 3.
Figure 6:
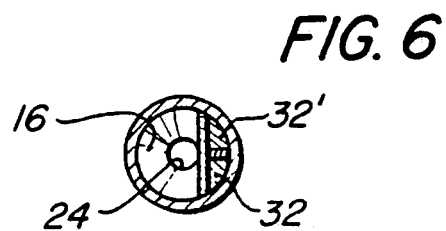
FIG. 6 is a cross-sectional view taken along line 6—6 of the catheter shown in FIG. 3.

The invention will now be described by reference to the various specific embodiments which are shown in the attached drawings. It is to be clearly understood that these embodiments are shown for purposes of illustration only and are not to be construed as limiting.

FIG. 1 shows a partial cutaway perspective view of a catheter of the invention, shown overall as (3), comprising an elongated tube (6) which is provided at its distal end with a conical tapered section (8). The latter tapers smoothly from its widest portion (10), having an external diameter equal to that of tube (6), to a tip (12) which has a diameter from about 1.8 to about 2.125 less than the external diameter of tube (6). As shown in the cutaway portion of FIG. 1 and more particularly in the cross-section of tube (6) shown in FIG. 2, an integrally formed septum (14) traverses the length of tube (6) and serves to separate the interior of tube (6) into a first lumen (16), a second lumen (18) and a third lumen (20). As shown in cross-section in FIG. 4, the septum (14) has a T-shaped cross-section wherein the cross-bar of the T (14b) defines with the associated wall of the tube (6) a semi-circular section which forms lumen (16). The stem (14a) of the T, taken with the associated wall of the tube (6) and the cross-bar of the T, defines two quadrantal sections which form the second and third lumens (18) and (20).

Referring again to FIG. 2, the first lumen (16) extends continuously from the proximal end (22) of tube (6) through the conical section (8) at the distal end to an opening (24) in the tip (12). As previously stated the septum (14) also extends continuously from the proximal end (22) of tube (6) throughout the length of the latter along the axis thereof until it reaches a point corresponding to the junction (10) of the tube and conical tapered section (8). At this point septum (14) begins to deviate at a 10 slight angle ($\theta$) from the direction of the axis (c) of tube (6) as shown in dotted lines in FIG. 2 wherein dotted line (d) is an extension of the direction of the distal portion of septum (14). The tip (12) and opening (24) are thereby aligned and centered on the central axis (c) of tube (6).

Second lumen (18) extends continuously from the distal end (22) of tube (6) to a series of openings (26), (28) and (30) in the sidewall of said tube. The portion of lumen (18) immediately below opening (30) is optionally blocked off by a filled portion (32) which extends all the way to tip (12). Correspondingly, third lumen (20), although not visible in cross-sectional view in FIG. 2, has a substantially identical configuration to that of lumen (18) and extends continuously from the distal end (22) of tube (6) to a series of openings in the wall of the tube at a location axially spaced from tip (12) by a distance corresponding to that for openings (26), (28) and (30). The portion of lumen (20) between the lowermost opening and tip (12) is optionally blocked off by a filled portion corresponding to (32) in lumen (18).

The distances by which the opening (30) in lumen (18) and the corresponding lowermost opening in lumen (20) are axially displaced from tip (12) are advantageously of the order of about 2 to about 5 millimeters and preferably are from about 2 to about 3 millimeters.

In a preferred embodiment the lumen (16) is provided with at least one and preferably at least two sidewall openings (34) and (36) in addition to the opening (24) in tip (12). The openings (34) and (36) are axially spaced from tip (12) by a distance which is significantly less than that for opening (30) in lumen (18) and its counterpart in lumen (20). Advantageously the openings in lumen (16) are located at a distance from tip (12) less than 0.3 times the distance of opening (30) from tip (12) and preferably less than about 0.25 times the latter distance.

A catheter having the configuration and internal structure illustrated in FIGS. 1 and 2 is fabricated in the following manner. A tube (6) is first produced, with septum (14) integrally formed therein, by extrusion of thermoplastic polymer material such as polyurethane, polyester, polypropylene and the like through an appropriate die using equipment and procedures well-known in the thermoplastic extrusion art. A suitable length of the extruded tube is cut and one end thereof is provided with a tip, having the construction shown in FIGS. 1 and 2, by heating the end in a tapered mold with a wire or rod of appropriate diameter inserted in the lumen corresponding to (16) to preserve opening (24) during the tapered process. The heat forming of the tip not only gives rise to the conical section (8), but also results in closing off the distal end of lumen (18) and the corresponding section of lumen (20). After the tapering operation the openings (26), (28), (30) in lumen (18), the corresponding openings in lumen (20), and openings (34) and (36) in lumen (16) are drilled in an appropriate manner.

Advantageously, the openings (34) and (36) are each aligned parallel to the axis of tube (6) at locations which approximate the midpoint of the semi-circular sidewall of the distal end of lumen (16). While two such openings are shown in the sidewall of lumen (16) in FIGS. 1 and 2, it is to be understood that the presence of the openings is optimal and that, if openings are present in this location they are not necessarily limited to one or two in number but may be greater in number. The openings (26), (28) and (30) in the sidewall of lumen (18) are advantageously located so that a radius drawn from the axis of tube (6) through said openings forms an angle x with the plane of member (14a) as shown in FIG. 4. Similarly, the corresponding openings in lumen (20) are located so that a radius drawn from the axis of tube (6) through said openings forms an angle y with the plane of member (14a) as also shown in FIG. 4. Advantageously, angles x and y are equal and have a value in the range of about 30° to about 45° and preferably from about 30° to about 35°. The number of openings in lumen (18) is shown as three for purposes of illustration only. This number can be as low as 1 or as high as 8 or more. Similar considerations apply to the number of openings in lumen (20).

In FIG. 3 there is shown a catheter in accordance with the invention having the configuration and structure of that shown in FIGS. 1 and 2 but being also fitted at its proximal end with a branching connector shown overall as (38). The connector has a tubular section with opening (40) in one end thereof and this tubular section bifurcates into sections (42) and (44) which are adapted to be fitted to additional tubing for delivery and/or removal of fluids. The connector (38) receives the proximal end (22) of tube (6) through opening (40). An extension (46) of septum (14) projects into tubular section (42) and enters into sealing engagement with the surface of divider (48) thereby sealing off lumen (16) and its connecting tubular section (44) from lumens (18) and (20) and their connecting tubular section (42). The attachment of connector (38) to the proximal end (22) of tube (6) in the above manner is achieved as follows. The circumferential portion of tube (6) at proximal end (22) is cut back to provide the projecting end (46) of the septum (14). The proximal end so modified is then mounted in an appropriate mold and the connector (38) is injection insert molded around said end using conventional techniques and employing thermoplastic material such as those illustrated hereinbefore.

In practice the catheter and connector shown in FIG. 3 is employed in dialysis and like techniques to introduce blood or other fluid into a vein or other cavity via connector section (44) and lumen (16) and thence through opening (24) and side openings (34) and (36).

At the same time fluid is withdrawn through openings (26), (28) and (30) and thence through lumens (18) and (20) and connector section (42).

Figure 7:
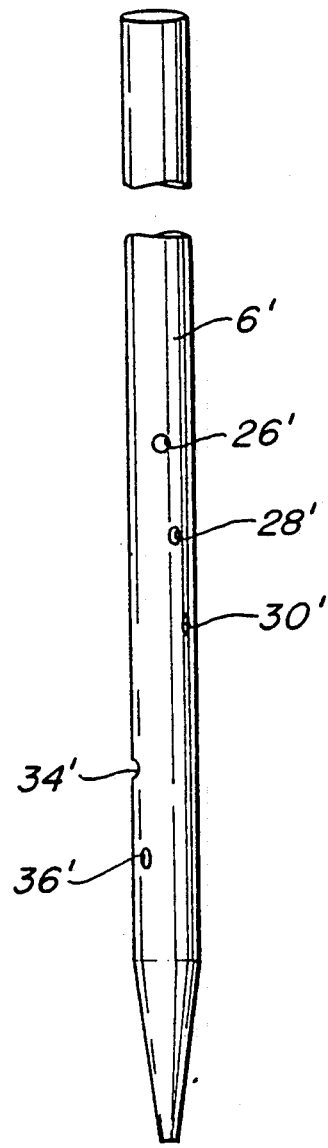
FIG. 7 is a side elevational view of another embodiment of a three-lumen catheter in accordance with the invention.

Another embodiment of a triple lumen catheter in accordance with the invention is shown in FIG. 7. This embodiment differs from that shown in FIG. 1 only in the manner in which the openings in the various lumens are aligned with respect to the axis of tube (6). In the embodiment of FIG. 1 the openings (34) and (36) in lumen (16) and (26) (28) and (30) in lumen (18) are aligned in a direction parallel to said axis. The corresponding openings (26') (28') (30') (34') and (36') in the catheter shown in FIG. 7 are located on paths which are spirally disposed with respect to said axis. The openings (not shown) on lumen (20) (also not shown) are also disposed in a similar spiral path.

As set forth hereinbefore, the various embodiments of the catheters of the invention, which have been described above, have been given for purposes of illustration and are not to be construed as limiting. As will be obvious to one skilled in the art, various changes and modifications can be made to the above embodiments without departing from the overall scope of the invention. Illustratively the cross-sectional shape and relative dimensions of the three-lumens (16), (18) and (20) can be altered, for example, to make them all of equal cross-sectional area or to make lumens (18) and (20) of unequal cross-sectional area. The size, shape and number of the sidewall openings in the various lumen can be varied to suit any particular end use to which the catheters are to be put. Other changes and modifications will be readily apparent to one skilled in the art.

It has been found unexpectedly that the three-lumen catheters of the invention can achieve higher fluid flow rates in dialysis and like procedures than can be achieved using dual lumen catheters having the same overall outside diameter. Thus, when dual lumen catheters, such as those hitherto employed, are placed in a vein or other vessel they have to be turned or manipulated to ensure non-occlusion of the side opening locations. Even so, after the lapse of a period of time the side openings tend to become occluded. The catheter has then to be repositioned or, in some cases, totally withdrawn, flushed with saline solution and repositioned in the vein or other vessel. In the case of the three lumen catheters of the invention there is significantly less chance of occlusion because of the increased number of openings and number of lumens on the fluid withdrawal side of the catheter. The catheters of the invention shown in FIG. 7 wherein the openings are located on spiral pathways show especially good performance and have an even lower chance of becoming occluded.

In addition the particular construction of the integral septum in the catheters of the invention provides addition reinforcement and resistance to deformation in the conical tapered tip. This is of particular importance in maintaining veins and other body cavities in inflated or expanded form while the catheter is in use and thereby avoiding reduction or stoppage in fluid flow through the opening in the tip of the catheter. Further, the presence of the integral septum greatly reduces the chance of kinking of the catheter while in use.

What is claimed is:

1. A three-lumen catheter comprising:
   an elongated unitary tube having an integral septum extending within the entire length of said tube and dividing the interior of said tube into first, second and third lumens, said integral septum having an approximately T-shaped cross-section;
   the outer circumference of said tube converging smoothly at its distal end to form a conical tapered tip;
   said first lumen extending from the proximal end of said tube continuously through said conical tapered tip to an opening at the apex of said tip, said first lumen for introducing fluid to a body cavity;
   each of said second and third lumens extending continuously from the proximal end of said tube to at least one opening in the sidewall thereof at a location axially spaced from said conical tip, both said second and third lumens for withdrawing fluid from a body cavity; and
   each of said second and third lumens having no opening through the apex of said conical tip.

2. A three-lumen catheter according to claim 1 wherein said first lumen has an approximately semi-cylindrical cross-section and said second and third lumens have approximately quadrantal cross-sections.

3. A three-lumen catheter comprising:
   an elongated unitary tube having an integral septum extending within the entire length of said tube and dividing the interior of said tube into first, second and third lumens;
   the outer circumference of said tube converging smoothly at its distal end to form a conical tapered tip;
   said first lumen extending from the proximal end of said tube continuously through said conical tapered tip to an opening at the apex of said tip, said first lumen for introducing fluid to a body cavity;
   each of said second and third lumens extending continuously from the proximal end of said tube to at least one opening in the sidewall thereof at a location axially spaced from said conical tip, both said second and third lumens for withdrawing fluid from a body cavity;
   each of said second and third lumens having no opening through the apex of said conical tip; and
   said first lumen having at least one opening in the sidewall thereof at its distal end at a location axially spaced from said conical tip a distance less than the openings in the sidewalls of said second and third lumens.

4. A three-lumen catheter according to claim 3 wherein there are at least two said openings in said sidewall of said first lumen, said openings being aligned on a path parallel to that of the axis of said elongated tube.

5. A three-lumen catheter according to claim 3 wherein there are at least two said openings in said sidewall of said first lumen and said openings are located on a path which is positioned spirally with respect to the axis of said elongated tube.

6. A three-lumen catheter according to claim 1 wherein the apex of said conical tip is substantially aligned with the axis of said elongated tube.

7. A three-lumen catheter according to claim 1 wherein the opening in the first lumen at the apex of said conical tip is substantially aligned with the axis of said elongated tube.

8. A three-lumen catheter according to claim 1 which also comprises a branching connector at the proximal end of said elongated tube connecting the latter to separate tubes one of which communicates with said first lumen to introduce fluid to the body cavity and the other of which communicates with said second and third lumens to withdraw fluid from the body cavity.

9. A three-lumen catheter comprising:
an elongated unitary tube having an integral septum extending within the entire length of said tube and dividing the interior of said tube into first, second and third lumens;
the outer circumference of said tube converging smoothly at its distal end to form a conical tapered tip;
said first lumen extending from the proximal end of said tube continuously through said conical tapered tip to an opening at the apex of said tip, said first lumen for introducing fluid to a body cavity;
each of said second and third lumens extending continuously from the proximal end of said tube to at least two said openings in the sidewall thereof at a location axially spaced from said conical tip, said openings being aligned on a path parallel to that of the axis of said elongated tube, both said second and third lumens for withdrawing fluid from a body cavity; and
each of said second and third lumens having no opening through the apex of said conical tip.

10. A three-lumen catheter comprising:
an elongated unitary tube having an integral septum extending within the entire length of said tube and dividing the interior of said tube into first, second and third lumens;
the outer circumference of said tube converging smoothly at its distal end to form a conical tapered tip;
said first lumen extending from the proximal end of said tube continuously through said conical tapered tip to an opening at the apex of said tip, said first lumen for introducing fluid to a body cavity;
each of said second and third lumens extending continuously from the proximal end of said tube to at least two said openings in the sidewall thereof at a location axially spaced from said conical tip, said openings being located on a path which is positioned spirally with respect to the axis of said elongated tube, both said second and third lumens for withdrawing fluid from a body cavity; and
each of said second and third lumens having no opening through the apex of said conical tip.

11. A three-lumen catheter comprising:
an elongated unitary tube having an integral septum extending within the entire length of said tube and dividing said tube into first, second and third lumens;
the outer circumference of said tube converging at its distal end to form a conical tapered tip;
said first lumen extending from the proximal end of said tube continuously through said conical tapered tip to an opening at the apex of said tip;
at least one opening in sidewall of said first lumen;
each of said second and third lumens extending continuously from the proximal end of said tube to a location axially spaced from said tip; and
each of said second and third lumens having at least two openings in the sidewall of said tube, said openings for each of said lumens being located on a path which is positioned spirally with respect to the axis of said tube.

12. The catheter of claim 11 comprising at least two openings in the sidewall of said first lumen.

13. The catheter of claim 12 wherein said openings in the sidewall of said first lumen are located on a path which is positioned spirally with respect to the axis of said tube.

14. The catheter of claim 13 comprising at least three openings in the sidewall of said first lumen.

15. The catheter of claim 14 wherein said openings in said first lumen are all spaced axially distally of said openings in said second and third lumens.

* * * * *